United States Patent
Matsabisa et al.

(10) Patent No.: US 8,586,112 B2
(45) Date of Patent: Nov. 19, 2013

(54) TREATMENT OF PARASITIC INFECTIONS IN HUMANS AND ANIMALS

(75) Inventors: Motlalepula Gilbert Matsabisa, Cape Town (ZA); William Ernest Campbell, Thornton (ZA); Peter Ian Folb, Cape Town (ZA); Peter John Smith, Cape Town (ZA)

(73) Assignees: South African Medical Research Council, Parow (ZA); University of Cape Town, Cape Town (ZA)

( * ) Notice: Subject to any disclaimer, the term of this patent is extended or adjusted under 35 U.S.C. 154(b) by 461 days.

(21) Appl. No.: 11/718,690

(22) PCT Filed: Nov. 2, 2005

(86) PCT No.: PCT/IB2005/003268
§ 371 (c)(1),
(2), (4) Date: Oct. 18, 2007

(87) PCT Pub. No.: WO2006/048734
PCT Pub. Date: May 11, 2006

(65) Prior Publication Data
US 2009/0304832 A1  Dec. 10, 2009

(30) Foreign Application Priority Data
Nov. 4, 2004  (ZA) .................................. 2004/8945

(51) Int. Cl.
*A61K 36/00*   (2006.01)
*A61K 31/34*   (2006.01)
*A61K 31/335*  (2006.01)
*C07D 307/00*  (2006.01)
*C07D 493/00*  (2006.01)

(52) U.S. Cl.
USPC ........... 424/773; 514/462; 514/468; 549/264; 549/299

(58) Field of Classification Search
None
See application file for complete search history.

(56) References Cited

U.S. PATENT DOCUMENTS 5,112,869 A * 5/1992 Watanabe et al. ............. 514/641

FOREIGN PATENT DOCUMENTS

JP   2004137897 A * 5/2004

OTHER PUBLICATIONS

Jeyadevan et al. "Antimalarial and Antitumor Evaluation of Novel C-10 Non-Acetal Dimers of 10-Beta-(2-Hydroxyethyl)deoxoartemisinin" J. Med. Chem. 2004, vol. 47, pp. 1290-1298.*

(Continued)

Primary Examiner — Chris R Tate
Assistant Examiner — Deborah Davis
(74) Attorney, Agent, or Firm — Winston & Strawn LLP

(57) ABSTRACT

The invention provides a process for the production of a substance or composition for the treatment, by therapy or prophylaxis, of parasitic infections, in particular malarial infections such as *Plasmodium falciparum* infections, of the human or animal body. The process comprises extracting the substance or composition from roots of the plant species *Dicoma anomala*, by an extraction using an organic solvent to obtain a liquid extract containing the substance or composition and removing the solvent from the liquid extract to leave a dried extract containing the substance or composition. The invention extends also to the use of the substance or composition in the manufacture of a medicament or preparation for such treatment of infections; to a substance or composition for use in such treatment of said infections; to compounds for use in such treatment of said infections; and to a method of treating said infections using such compounds.

12 Claims, 4 Drawing Sheets

(56) References Cited

OTHER PUBLICATIONS

Bohlmann et al. ("Dimeric guaianolides and other constituents from *Gochnatia* species", Phytochemistry (1986), vol. 25(5), pp. 1175-1178, Abstract Only).*

Tutin et al., "Chemical Examination of Dicoma Anomala" The Pharmaceutical Journal and Pharmacist, vol. 90, May 17, 1913., pp. 694-696.*

Bohlmann, Ferdinand, Singh, Pahup and Jakupovic, Jasmin; Germacranolides From Dicoma Tomentosa; Phytochemistry; 1982; pp. 2122-2124; vol. 21, No. 8; Pergamon Press Ltd.; Great Britain.

Bohlmann, Ferdinand and Van, Ngo Le; New Germacranolides From Dicoma Anomala; Phytochemistry; 1978; pp. 570-571; vol. 17; Pergamon Press Ltd.; Great Britain.

Appendino, Giovanni, Jakupovic, Jasmin and Jakupovic, Sven; Sesquiterpenoids From Pallenis Spinosa; Phytochemistry; 1997; pp. 1039-1043; vol. 46, No. 6; Pergamon Press Ltd.; Great Britain.

Mokhobo, K.P.; Herb Use and Necrodegenerative Hepatitis; South African Medical Journal; Jul. 3, 1976; pp. 1096-1099.

Nyazema, N.Z.; Ndamba; J.; Anderson, C.; Makaza, N. and Kaondera, K.C.; The Doctrine of Signatures or Similitudes: A Comparison of the Efficiency of Praziquantel and Traditional Herbal Remedies Used for the Treatment of Urinary Schistosomiasis in Zimbabwe; International Journal of Pharmacognosy; 1994; pp. 142-148; 32, No. 2; Swets & Zeitlinger.

Hedberg, Inga and Staugard, Frants; Traditional Medicinal Plants; Traditional Medicine in Botswana; 1989; Title Page & p. 109; Ipelong Publishers; Broadhurst.

Patent Cooperation Treaty; International Preliminary Report on Patentability for PCT/IB2005/003268; Mar. 26, 2007; 16 pgs.; European Patent Office; Berlin.

Ramathal, Dorothy C. & Ngagssapa, Olipa D.; Medicinal Plants Used by Rwandese Traditional Healers in Refugee Camps in Tanzania; Pharmaceutical Biology; 2001; pp. 132-137; vol. 39, No. 2.

Chinemana, F., Drummond, R.B., Mavi, S. & De Zoysa, I.; Indigenous Plant Remedies in Zimbabwe; Journal of Ethnopharmacology, 1985; pp. 159-172; Elsevier Scientific Publishers Ireland Ltd.; Ireland.

Dzerefos, Catherine M. & Witkowski, E.T.F., Density and Potential Utilization of Medicinal Grassland Plants From Abe Bailey Nature Reserve, South Africa; Biodiversity and Conservation; 2001; pp. 1875-1896; Kluwer Academic Publishers; Netherlands.

Zdero, C. & Bohlmann, F.; Sesquiterpene Lactones From *Dicoma* Species; Phytochemistry; 1990; pp. 183-187; vol. 29, No. 1; Pergamon Press plc; Great Britain.

Bohlmann, Ferdinand, Singh, Pahup & Jakupovic, Jasmin; New Germacranolides and Other Sesquiterpene Lactones From *Dicoma* Species; 1982, pp. 2029-2033; vol. 21, No. 8; Pergamon Press Ltd.; Great Britian.

Clarkson, Cailean, Maharaj, Vinesh J., Crouch, Neil R., Grace, Olwen M., Pillay, Pamisha, Matsabisa, Motlalepula G., Bhagwandin, Niresh, Smith, Peter J. & Folb, Peter I.; In Vitro Antiplasmodial Activity of Medicinal Plants Native to or Naturalised in South Africa; 2004; pp. 177-191; Journal of Ethnopharmacology; Elsevier Ireland Ltd.; Ireland.

Steenkamp, V., Mathivha, E., Gouws, M.C. & Van Rensburg, C.E.J.; Studies on Antibacterial, Antioxidant and Fibroblast Growth Stimulation of Wound Healing Remedies From South Africa; 2004; pp. 353-357; Journal of Ethnopharmacology; Elsevier Ireland Ltd.; Ireland.

Chinemana, F., Drummond, R.B., Mavi, S. & De Zoysa, I.; Indigenous Plant Remedies in Zimbabwe; Journal of Ethnopharmacology; 1985; pp. 159-172; vol. 14; Elsevier Scientific Publishers Ireland Ltd.; Ireland.

Ramathal, Dorothy C. & Ngassapa, Olipa D.; Medicinal Plants Used by Rwandese Traditional Healers in Refugee Camps in Tanzania; Pharmaceutical Biology; 2001; pp. 132-137; vol. No. 39, No. 2; Swets & Zeitlinger.

* cited by examiner

TREATMENT OF PARASITIC INFECTIONS IN HUMANS AND ANIMALS

This application is a §371 U.S. national phase application of International Application No. PCT/IB2005/003268, filed Nov. 2, 2005, and claims the benefit of South African Application No. 2004/8945, filed Nov. 4, 2004. Both of these prior applications are incorporated herein by reference in their entirety.

THIS INVENTION relates to the treatment of parasitic infections in humans and animals. More particularly, the invention relates to a substance or composition, and to one or more compounds for use in such treatment, which may be therapeutic or prophylactic, to a method of such treatment, and to a process for the production of such substance or composition and compounds, for the treatment of parasitic infections, the substance or composition and compounds, the methods of treatment and the process of production all being useful for, but not limited to, the prophylaxis or treatment of malarial parasitic infections by *Plasmodium* species, in particular *P. falciparum*.

According to the invention there is provided a process for the production of a substance or composition for the treatment, by therapy or prophylaxis, of parasitic infections, in particular malarial infections such as *Plasmodium falciparum* infections, of the human or animal body, the process comprising the steps of:

extracting the substance or composition from a starting material comprising plant roots of the plant species *Dicoma anomala*, by subjecting the plant root starting material to extraction using an organic solvent to obtain a liquid extract containing the substance or composition; and removing the solvent from the liquid extract to leave a dried extract containing the substance or composition.

While the extraction may be a cold (room temperature) extraction, it may be a hot (Soxhlet) extraction. Thus the extraction may be a hot extraction carried out at an elevated temperature in the range 35-140° C., for example 35-50° C. Conveniently, however, the extraction is a cold extraction carried out at a temperature of at most 40° C.

The plant root starting material may be a solid plant material in a finely divided form, having a particle size not exceeding 100 µm, preferably not exceeding 10 µm. Thus, in other words, the plant root starting material may be in powdered form having a particle size of at most 100 µm, preferably at most 10 µm.

One or more organic liquids may be used as the solvent for the extraction, either separately in sequence, or as mixtures or blends. The solvent may be a polar solvent having a polarity index in the range 0.00-5.00. Preferably each liquid or blend of liquids used as the solvent thus may have a polarity index of at least 0.00 and at most 5.00. In particular, the solvent may have a polarity index of 1.0-4.8 and may comprise at least one member selected from the group consisting of the solvents set forth in the following table, Table 1, in which the polarity indices of the solvents are also listed:

TABLE 1

| Solvent | Polarity Index |
| --- | --- |
| Benzene | 2.7 |
| n-Butanol | 3.9 |
| Butyl Acetate | 4.0 |
| Carbon Tetrachloride | 1.6 |
| Chloroform | 4.1 |
| 1,2 Dichloroethane | 3.5 |
| Dichloromethane | 3.1 |

TABLE 1-continued

| Solvent | Polarity Index |
| --- | --- |
| Dioxane | 4.8 |
| Ethyl Acetate | 4.4 |
| di-Ethyl Ether | 2.8 |
| Methyl-t-Butyl Ether | 2.5 |
| Methyl Ethyl Ketone | 4.7 |
| n-Propanol | 4.0 |
| iso-Propanol | 3.9 |
| di-iso-Propanol | 2.2 |
| Tetrahydrofuran | 4.0 |
| Toluene | 2.4 |
| Trichloroethylene | 1.0 |
| Xylene | 2.5 |

A particularly preferred solvent has been found to be dichloromethane ($CH_2Cl_2$).

The process may include subjecting the plant root starting material to a preliminary extraction, using a non-polar organic solvent having a polarity index of less than 3.90, preferably a polarity index in the range 3.10-3.50, followed by drying to evaporate residual non-polar solvent from the solid plant material, and then subjecting the dried plant root material, from which the non-polar solvent has been removed, to the extraction, to obtain the liquid extract containing the substance or composition. The preliminary extraction may be carried out with the non-polar solvent at a temperature of 15-30° C., the drying being carried out at a temperature not exceeding 40° C., and both extractions being carried out to exhaustion. In particular, the process may include subjecting the dried extract containing the substance or composition to removal of tannin therefrom using a polymer of an organic amide.

Thus, in a preferred embodiment of the process of the present invention the powdered plant root starting material is subjected to a preliminary extraction, which may be substantially to exhaustion, at room or ambient temperature (15-30° C.), using a non-polar solvent such as hexane, the hexane extract being discarded and residual hexane in the solid plant material being removed by evaporation by drying the solid plant material at a temperature not exceeding 40° C. In this embodiment of the process the dried plant material, from which the hexane has been removed, will then be subjected to a further extraction, to obtain the pharmaceutically active constituents of the plant material, the further extraction also preferably being to exhaustion, using the selected polar solvent, such as dichloromethane. The dichloromethane, after the further extraction, may then be removed at a temperature not exceeding 40° C. from the plant material to provide a dichloromethane extract of the plant material and to leave a dried solid plant residue, which is discarded. The dichloromethane extract may then be subjected to removal of tannin therefrom using Polyamide S, i.e. a polymer of an organic amide available from Riedel de Haen.

*D. anomala* is a small and low-growing herb with small, stiff and bluish-grey leaves. It has a protea-like head of flowers which opens in mid-summer. The herb grows flat along the ground on North-facing rocky hillsides. It prefers full sun and well-drained soil and has been propagated from seed only. *D. anomala* is distributed from the Eastern Cape province in South Africa, through the KwaZulu-Natal-, Free State-, Gauteng-, Mpumalanga- and Northern provinces in South Africa, and into Zimbabwe and Lesotho. It is also found in Botswana, Namibia and thence to Zambia and Uganda in the North.

For the purpose of the present invention, the Applicant has employed *D. anomala* roots collected from the Morifi and Mohales' hoek areas in Lesotho, from the Reitz area in the Free State, and from the Sikhukhuni area in the Northern province. Roots bought from herb markets in Durban, in the KwaZulu-Natal province, have also been investigated. The *D. anomala* used has been identified by voucher specimen No. 98142 deposited at the Bolus Herbarium at the University of Cape Town, in the Western Cape Province of South Africa.

The dichloromethane extract obtained as described above from *D. anomala* was found, after the tannin removal, to have substantial antiplasmodial activity which outweighs its cytotoxicity to an extent which indicates that it comprises a substance or composition suitable for the therapeutic or prophylactic treatment of malaria in the human or animal body.

Thus, the dichloromethane extract of *D. anomala* was found to have plasmocidal effects both on the chloroquine-sensitive D10 strain and on the chloroquine-resistant FAC8 strain of *P. falciparum*, with $IC_{50}$ values of 2000 ng/ml and 6000 ng/ml for the D10 and FAC8 strains respectively. The applicant found the antiplasmodial activity of the dichloromethane extract to exceed the cytotoxic activity thereof with regard to a number of human cancer cell lines, by a factor of 10 (i.e. by an order of magnitude). In this regard the dichloromethane extract (and the sesquiterpenes displaying antiplasmodial activity discussed hereunder) were found to have an antiplasmodial selectivity index of about 10 on a number of cancer cell lines. The antiplasmodial selectivity index (SI antiplasmodial) can be expressed by:

SI antiplasmodial=$IC_{50}$ antiplasmodial/$IC_{50}$ cytotoxicity.

After fractionating of the dichloromethane extract into a number of fractions and after testing the antiplasmodial activity of these fractions, it was found that antiplasmodial activity is confined to those fractions which contain members of a series of asymmetrical sesquiterpene dimers whose molecular masses differed from one another by 18 atomic mass units (characteristic of several losses of water —$H_2O$), from a minimum molecular mass of 230 up to a maximum molecular mass of 539.

In particular, antiplasmodial activity was found to be present in the fraction of the *D. anomala* dichloromethane extract which contains two asymmetrical sesquiterpene dimers having molecular masses respectively of 506.23879 atomic mass units and 508.23980 atomic mass units, these masses differing from each other substantially by 2 atomic mass units. The molecular ratio of the heavier compound to the lighter compound (i.e. of the 508.23980 atomic mass unit compound to the 506.23879 atomic mass unit compound) was found to be 1:3, as determined by their $^1H$ spectra, liquid chromatography-mass spectroscopy (LC-MS) and by atmospheric pressure chemical ionization high resolution mass spectroscopy (APCI HRMS). The minor (heavier) of the two compounds was shown by APCI HRMS to have a highest molecular mass of $M^++1=509.2545$ atomic mass units, consistent with the empirical molecular formula of $C_{30}H_{36}O_7$; while the major (lighter) compound had a highest molecular mass of $M^++1=507.2388$ atomic mass units, determined by APCI ARMS, consistent with an empirical molecular formula of $C_{30}H_{34}O_7$.

The compounds of formulae $C_{30}H_{36}O_7$ or $C_{30}H_{34}O_7$ were found to have antiplasmodial activity against the chloroquine-sensitive (D10) strain of *P. falciparum* with an $IC_{50}$ value of 200 ng/ml. This amounted substantially to a 10-fold increase in activity over that of the crude dichloromethane extract.

The dichloromethane extract of *D. anomala* was also tested in vitro against Gram negative bacteria and Gram positive bacteria and was found to be bactericidally active at minimum effect concentrations (MEC) of 250 µg/ml, which is an indication of bacteriocidal activity against bacterial infections and utility in combatting bacterial infections.

When the dichloromethane extract of *D. anomala* was tested for toxicity in test animals, no toxicity was found when the extract was administered at levels of up to 100 mg/kg of body mass, and no morphological changes were found to the spleen, liver or kidneys of test animals. Toxicology was determined by death, hair-straightening as a sign of loss of well-being, and loss of body weight as a sign of loss of well-being. In respect of these parameters the test animals were found not to deviate from control animals.

The active sesquiterpene compounds were concentrated employing solid phase extraction (SPE), using 10 g C-18 end capped (EC) 70 ml Isolute cartridges. Cartridges were conditioned thrice with methanol and then thrice with water, followed by sample loading at 4 mg/ml (i.e. 200 mg/50 ml), followed in turn by percolation to obtain Fraction 1, by washing with 100% water to obtain Fraction 2, and by sequential cartridge-elution with 50 ml mixtures of MeCN and water in the proportions given in the following table, Table 2, to obtain Fractions 3-12:

TABLE 2

| | Eluant | | | | | | | | | |
|---|---|---|---|---|---|---|---|---|---|---|
| | 1 | 2 | 3 | 4 | 5 | 6 | 7 | 8 | 9 | 10 |
| Fraction | 3 | 4 | 5 | 6 | 7 | 8 | 9 | 10 | 11 | 12 |
| % MeCN in mixture (by volume) | 10% | 20% | 30% | 40% | 50% | 60% | 70% | 80% | 90% | 100% |

Analytical high pressure liquid chromatography (HPLC) separations and preparative scale purification were carried out on the active sesquiterpene compounds using as the mobile phase mixtures of MeCN (0.05% by volume tetrafluoroacetic acid (TFA)) and water (0.05% by volume TFA), and using a gradient of 30-100% MeCN in 40 minutes. The flow rates used were 1 ml/minute for analysis and 50 ml/minute for preparative scale purification. The column used was a Phenomenex Prodigy—using ODS 2-type silica, C-18 and 5 µm (particle size) (4.6×150 mm); and the ultra-violet (UV) range for data collection was 200-600 nm. The pure compounds had a maximum absorbance (λ max) at a wavelength of 225 nm. Sample strength was 10 mg/t and injection volume was 50 µl for analytical separation and 500 ml for preparative separation.

With regard to structural elucidation of the active sesquiterpene compounds, mass spectra were obtained at the same time as the HLPC run, using a Thermo Quest LCQ (Finnegan) high resolution mass spectrometer connected inline with the high pressure liquid chromatograph. The liquid chromatograph/mass spectrometer set-up was equipped with both electrospray ionization (ESI) and atmospheric pressure chemical ionization (APCI) probes and an ion trap.

Nuclear magnetic resonance (NMR) spectra (1H, 13C, correlation spectroscopy (COSY), distortionless enhancement by polarization transfer (DEPT)-135), heteronuclear multiple quantum coherence (HMQC), and heteronuclear multiple bond quantum correlation (HMBC) were recorded on a Bruker-DR X-400 spectrometer (1H:400.13 MHz, 13C: 100.62 MHz) and a Bruker-DRX-500 spectrometer with inverse detection and z-gradient equipment (1H:500.13 MHz, 13C:125.77 MHz) at 23° C. in CDCI3. The chemical shifts (δ) were related to the signal of the residual solvent.

The asymmetrical sesquiterpene antiplasmodially active dimer compounds of the *D. anomala* extract of the present conversion have been found to be no more than sparingly soluble and the bioavailability of the compounds will depend on such routes of the administration as are found to be possible (orally, rectally and intravenously). In principle formulation of the active compounds into one or more of capsules, tablets, syrups, injectable liquids and herbal tinctures (optionally stabilized) is possible, the formulation or formulations selected depending on bioavailability and pharmacokinetics of the compounds.

Furthermore, the Invention extends also to the use of a substance or composition in the manufacture of a medicament or preparation for the therapeutic or prophylactic treatment of parasitic infections, in particular malarial infections such as *P. falciparum* infections, of the human or animal body, the substance or composition comprising an organic solvent root extract of a plant of the species *D. anomala*.

Further, the invention extends also to the use of a substance or composition in the manufacture of a medicament or preparation for the therapeutic or prophylactic treatment of parasitic infections, in particular malarial infections such as *P. falciparum* infections, of the human or animal body, the substance or composition comprising at least one asymmetrical sesquiterpene dimer having a molecular mass in the molecular range 230-539 atomic mass units.

The substance or composition may comprise a plurality of asymmetrical sesquiterpene dimers having molecular masses in the molecular range 230-539 atomic mass units.

The substance or composition may comprise at least one asymmetrical sesquiterpene dimer, having a structural formula as shown in any one of FIGS. 2 and 6-9 as described hereunder, or it may comprise at least one derivative of an asymmetrical sesquiterpene dimer having a structural formula as shown in any one of FIGS. 2 and 6-9, the derivative being selected from the group consisting of:

derivatives in which one or more of any α-methylene groups forming part of γ-lactones and any exocyclic methylene groups in the dimer are reduced to methyl groups;

derivatives in which one or more of any γ-lactones are opened by hydrolysis to produce hydroxy-carboxylic acids;

derivatives in which one or more of any carboxyl groups in the dimer are reduced to methylene groups;

derivatives in which one or more of any primary alcohol groups in the dimer are oxidized to aldehyde groups; and derivatives in which one or more of any secondary alcohol groups in the dimer are converted to ketone groups and acetate groups.

The invention extends also to the plant extracts (and to the antiplasmodially active sesquiterpene compounds contained therein) as substances or compositions for the treatment, by therapy or prophylaxis, of bacterial and in particular plasmodial (malarial) infections of the animal and particularly the human body.

Thus, more particularly, the invention extends further to a substance or composition for use in a method of treatment or prophylaxis of parasitic infections of the human or animal body, in particular malarial infections such as *P. falciparum* infections, by administering an effective amount of said substance or composition to the human or animal body, said substance or composition forming part of an organic solvent root extract extracted from roots of plants of the species *D. anomala*.

The substance or composition may comprise at least one asymmetrical sesquiterpene dimer having a molecular mass in the molecular mass range 230-539 atomic mass units. In particular, the substance or composition may comprise at least one asymmetrical sesquiterpene dimer having an empirical formula selected from the group consisting of C30H36O7 (with a molecular mass in the range 508.239-508.240 atomic mass units) and C30H34O7 (with a molecular mass in the range 506.238-506.239 atomic mass units). The substance or composition may comprise a plurality of asymmetrical sesquiterpene dimers having molecular masses in the molecular range 230-539 atomic mass units.

The invention extends further also to a substance or composition for use in a method of treatment or prophylaxis of parasitic infections, in particular malarial infections such as *P. falciparum* infections, of the human or animal body by administering an effective amount of said substance or composition to the human or animal body, the substance or composition comprising at least one asymmetrical sesquiterpene dimer having a molecular mass in the molecular range 230-539 atomic mass units.

The substance or composition may comprise a plurality of asymmetrical sesquiterpene dimers having molecular masses in the molecular range 230-539 atomic mass units.

In particular, as indicated above, the substance or composition may comprise at least one asymmetrical sesquiterpene dimer having an empirical formula selected from the group consisting of $C_{30}H_{36}O_7$ (with a molecular mass in the range 508.239-508.240 atomic mass units) and $C_{30}H_{34}O_7$ (with a molecular mass in the range 506.238-506.239 atomic mass units).

The asymmetrical sesquiterpene dimers may be present in the aforementioned substance or composition at a concentration of at least 0.08% by mass, e.g. at least 0.2% by mass. Preferably, the concentration of the asymmetrical sesquiterpene dimers is at least 50% by mass, more preferably at least 70% and most preferably at least 99% by mass.

In particular, the substance or composition may be in a form selected from the group consisting of capsules, tablets, syrups, injectable preparations, herbal tinctures and suppositories. Thus the substance or composition may be for use in a method of treatment of prophylaxis in which the administering of the substance or composition is in unit dosage form. Preferably, the administering of the substance or composition may be such as to attain an effective serum concentration, by mass of the dimers, in the human or animal body. More particularly, the administering of the substance or composition may be at an effective daily dosage rate, the rate being dependent on the body mass of the subject.

Preferably the extract is one resulting from a cold or hot extraction performed on the *D. anomala* roots using an organic solvent, in particular dichloromethane, having a polarity index of 0-5, for example the solvents set forth in Table 1. When the substance or composition comprises the sesquiterpene compounds from the series whose molecular masses differ by 18 atomic mass units from one another from the series, in particular the two asymmetrical sesquiterpene dimers having molecular masses of 506.23879 atomic mass units and 508.23980 atomic mass units respectively, in more or less refined form, so that they are present at concentrations greater than those present in the extracts, in particular the dichloromethane extracts, of *D. anomala*, the active compounds may form at least 0.2% by mass of the substance or composition, preferably at least 50%, more preferably at least 70% and most preferably at least 99%.

The substance or composition may comprise at least one asymmetrical sesquiterpene dimer having a structural formula as follows:

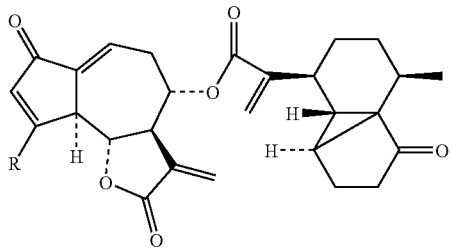

Instead or in addition, the substance or composition may comprise at least one asymmetrical sesquiterpene dimer having a structural formula as follows:

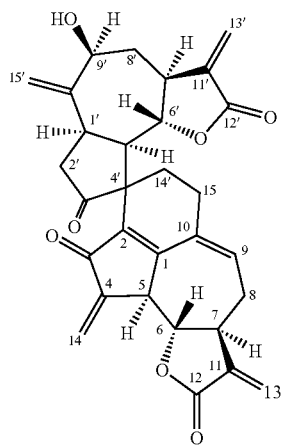

Instead or in addition, the substance or composition may comprise at least one asymmetrical sesquiterpene dimer having a structural formula as follows:

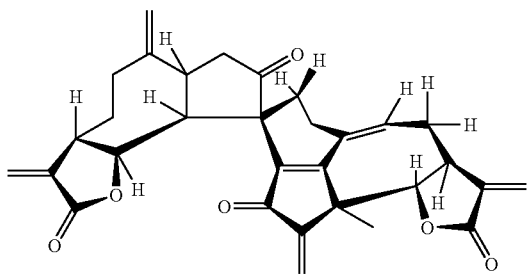

Instead or in addition, the substance or composition may comprise at least one asymmetrical sesquiterpene dimer having a structural formula as follows:

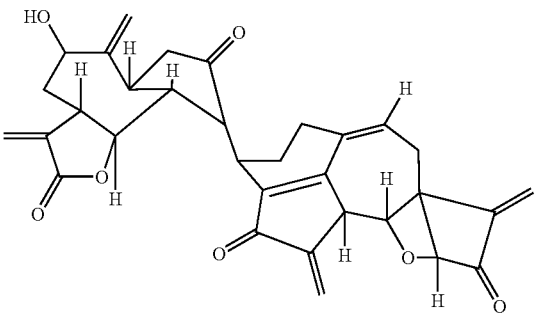

Instead or in addition, the substance or composition may comprise at least one asymmetrical sesquiterpene dimer having a structural formula as follows:

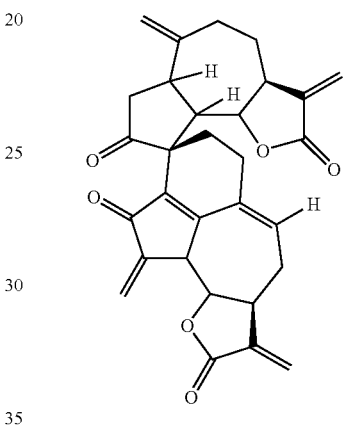

The invention extends to an asymmetrical sesquiterpene dimer which has a structural formula as shown in any one of FIGS. 2 and 6-9.

The invention extends further to a derivative which can be obtained from an organic solvent root extract of a plant of the species *D. anomola*, the derivative being of an asymmetrical sesquiterpene dimer which can be obtained from an organic solvent root extract of a plant of the species *D. anomola*.

The derivative may be a derivative of a said dimer which has a molecular mass in the molecular mass range 230-539 atomic mass units.

The derivative may be selected from the group consisting of:
derivatives in which one or more of any α-methylene group forming part of γ-lactones and any exocyclic methylene groups in the dimer are reduced to methyl groups;
derivatives in which any γ-lactones in the dimer are opened by hydrolysis to produce hydroxyl-carboxylic acids;
derivatives in which one or more of any carboxyl groups in the dimer are reduced to methylene groups;
derivatives in which one or more of any primary alcohol groups in the dimer are oxidized to aldehyde groups; and
derivatives in which one or more of any secondary alcohol groups are converted to ketone groups and acetate groups.

The derivative may be a derivative of a said dimer which has a structural formula as shown in any one of FIGS. 2 and 6-9.

The invention furthermore extends to a method of treatment or prophylaxis of parasitic infections, in particular malarial infections such as *P. falciparum* infections, of the human or animal body, the method comprising administering to a human or animal subject an effective amount of a substance or composition comprising an organic solvent root extract extracted from roots of plants of the species *D. anomala*.

The invention furthermore extends also to a method of treatment or prophylaxis of parasitic infections, in particular malarial infections such as *P. falciparum* infections, of the human or animal body, the method comprising administering to a human or animal subject an effective amount of a substance or composition comprising at least one asymmetrical sesquiterpene dimer having a molecular mass in the molecular range 230-539 atomic mass units.

The substance or composition may comprise a plurality of asymmetrical sesquiterpene dimers having molecular masses in the molecular range 230-539 atomic mass units.

The administering of the substance or composition may be in unit dosage form. In particular, the administering of said substance or composition may be such as to attain an effective serum concentration, by mass of the dimers, in the human or animal body. More particularly, the substance or composition may be administered at an effective daily dosage rate, the rate being dependent on the body mass of the subject.

The structure of the asymmetrical sesquiterpene dimers forming the active ingredients of the present invention will be discussed with reference to the following schematic drawings, in which.

Figure 2:
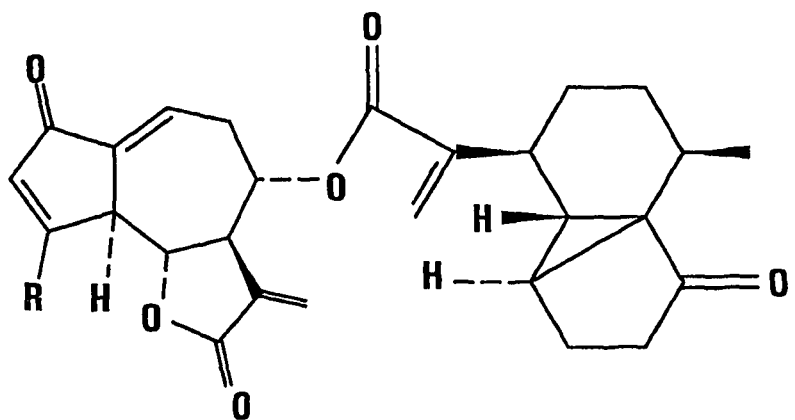
FIG. 2 shows a general schematic structural representation of the dimers of the present invention.
Figure 3:
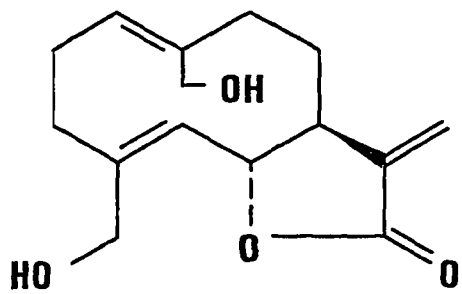
Figure 4:
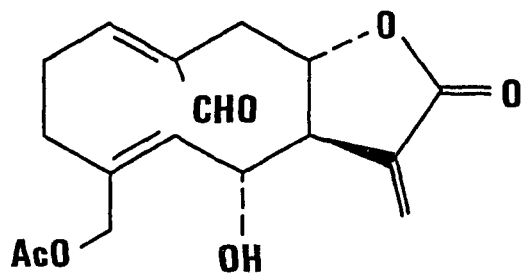
Figure 5:
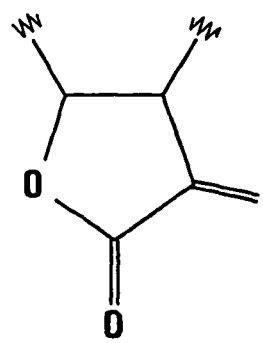

FIGS. 3 and 4 respectively show schematic structural representations of monomers into which the dimers of FIG. 2 can be split;

FIG. 5 shows a schematic structural representation of an α-methylene-γ-lactone forming a substituent in the dimers and monomers of FIGS. 2-4; and FIGS. 6-9 respectively show structural formulae of certain asymmetrical sesquiterpene dimers of the present invention.

Figure 1:
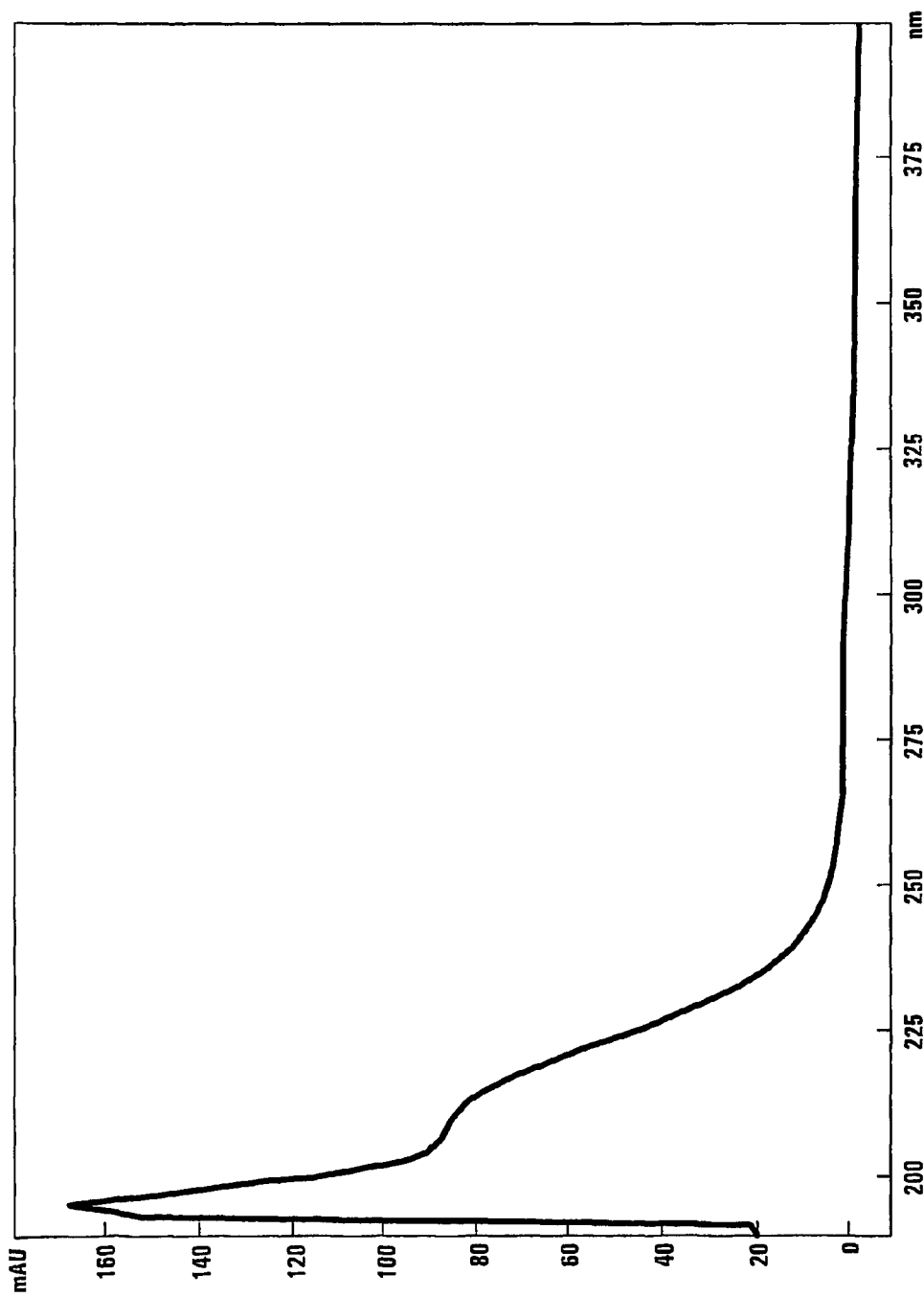
FIG. 1 shows a plot of milli-absorbence units (mAU) against wavelength in nanometers (nm)

FIG. 1 shows the UV spectrum of two of the active asymmetrical sesquiterpene dimers of the present invention, i.e. the asymmetrical sesquiterpene dimers, in solution in dichloromethane and at a concentration in total of 0.2%, in the ratios in which the dimers in question are present in the extracts from *D. anomala*, and in *D. anomala* itself, the dimers in question being those discussed above and having molecular masses best represented as 506.23879 atomic mass units and 508.23980 atomic mass units respectively.

FIG. 2 shows the best representation of a structural formula which the applicant is presently able to provide for both the above dimers.

FIGS. 3 and 4 show respectively monomers into which the dimers of FIG. 2 can be split, and it will be noted that the dimer and the monomers each contain the α-methylene-γ-lactone of FIG. 5.

FIGS. 6-9 respectively show structural formulae of four additional asymmetrical sesquiterpene dimers, different from the two illustrated by FIG. 2, also forming active ingredients of the present invention.

Without being bound by theory, the applicant believes that it may be possible to obtain a number of semi-synthetic derivatives of the asymmetrical sesquiterpene dimers obtained from *D. anomala*. Thus, the α-methylene groups of the γ-lactones, as well as any other exocyclic methylene groups in the dimers can be reduced to methyl groups as follows:

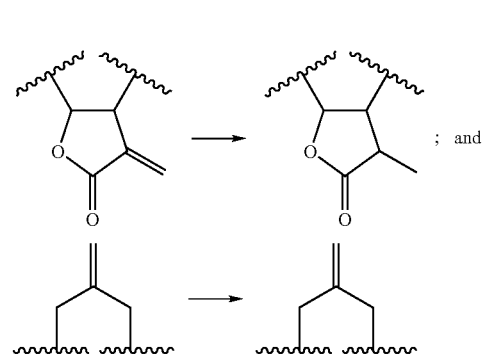

The γ-lactones can be opened by hydrolysis to produce hydroxy-carboxylic acids as follows:

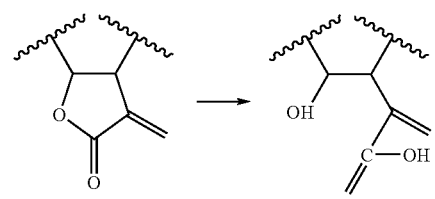

Carbonyl groups can be reduced to methylene groups as follows:

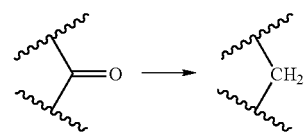

Primary alcohols can be oxidised to aldehydes, which can be further derivatised as follows:

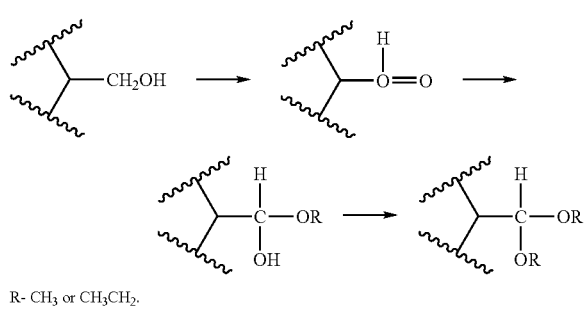

R- $CH_3$ or $CH_3CH_2$.

Finally, secondary alcohols can be converted to ketones and acetates as follows:

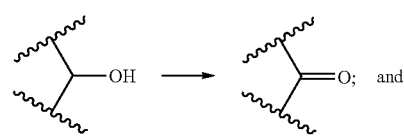

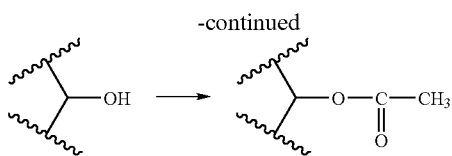

It is believed that at least some of the derivatives of the asymmetrical sesquiterpene dimers obtainable as set forth above can have anti-malarial activity, possibly enhanced antimalarial activity compared with that of the dimers derived from *D. anomala*.

The invention will now be described, by way of non-limiting illustration, with reference to the following worked Examples.

EXAMPLE 1

Plant material from *D. anomala* was authenticated and a voucher specimen [No. 98142] was deposited with regard to the plant material at the Bolus Herbarium of the University of Cape Town. The plant material was washed free of the fungal growth, bacterial growth and/or soil, and was dried at room temperature away from direct sunlight. The plant material was then ground, using a plant grinder, to a particle size of at most 10 μm. The ground plant material was stored in dry cardboard boxes in a well-ventilated store prior to extraction.

To carry out cold extractions on the plant material, 500 g batches of ground dried plant material were weighed and extracted using 5 l cold (room temperature) dichloromethane. The extraction was carried out over a period of 24 hours, accompanied by agitation/shaking at 130 rpm, after with the extraction mixture was filtered, and a further 5 l cold dichloromethane was added for a further extraction cycle. The extraction cycles were repeated until the material was extracted to exhaustion, after which the filtrate obtained from each cycle was pooled, and the dichloromethane was removed by rotary evaporation at most 40° C., to leave the plant extract. The extract was then dried under a fume hood away from direct sunlight, after which yields were determined, and the dried extract was screened for antimalarial activity.

Extracts which showed no antimalarial activity were discarded, and those with antimalarial activity had tannins and polyphenolic compounds removed therefrom by dissolving 200 mg of the dried dichloromethane extract in 100 ml methanol to which 5 g of Polyamide S (an organic amide polymer) powder was added, followed by thorough mixing and filtration under vacuum using a Buchner funnel. The residue was washed with a further 100 ml of methanol, followed by a further said filtration, after which the methanol filtrates containing the tannin-free dissolved extract were pooled. The methanol was evaporated under vacuum and the tannin-free extract was dried under a fume hood.

The residue remaining after the methanol extraction was washed twice with 20 ml batches of N,N-dimethylformamide (DMF) to extract the tannin material from the residue. The DMF was then removed under vacuum and the remaining extract was dried under a fume hood.

The dichloromethane extract, the methanol extract and the DMF extract were tested for antimalarial activity, and, except for the dichloromethane extract, were discarded.

The dichloromethane extract was purified by a solid phase extraction (SPE), C-18 end capped SPE reverse phase cartridges being used, having a capacity of 10 g and 70 ml. An amount of 200 mg of the dried dichloromethane extract, from which tannins and polyphenolic compounds had been removed was prepared for the SPE extraction by complete dissolution thereof in 15 ml of MeCN, the solution being centrifuged for 15 minutes at 13000 rpm, after which the supernatant liquid was decanted. Then 35 ml of distilled de-ionized water was added to the supernatant liquid, followed by centrifuging for 15 minutes at 13000 rpm, followed by decanting and filtration of the supernatant liquid for use in the SPE.

The SPE cartridges were conditioned by washing thrice with 50 ml of MeCN, followed by washing thrice with 50 ml of distilled de-ionized water. Sample loading at 4 mg/ml was carried out by loading the 50 ml solution obtained from the 200 mg extract on each column. To each column a vacuum was gently applied after a one minute interval, to obtain a percolate which was collected as a first fraction. The percolate was concentrated by freeze drying. The cartridges were each then washed five times with 50 ml aliquots (250 ml in total) of de-ionized water, the water then being removed by freeze drying, to leave a second or washed fraction.

Cartridge elution was carried out by eluting each cartridge five times with 50 ml aliquots (250 ml in total) of solutions of MeCN mixed with water, in which the concentrations of MeCN and water were varied stepwise as shown hereinabove in Table 2, in which Fractions 3-12 are shown, Fractions 1 and 2 being the first and second fractions referred to above derived respectively from sample loading and cartridge washing.

For testing the plant extracts, malaria parasites of the species *P. falciparum* were used, which had been maintained in culture flasks at 37° C. in an atmosphere comprising, by volume, 3% oxygen, 4% carbon dioxide and 93% nitrogen, prior to testing of the plant extracts. The parasites were cultured in a culture medium which was changed daily, and was diluted with fresh red blood cells every 2-3 days so that at least 5% of the red blood cells were infected at any time. Parasitemia was observed by means of Giemsa R66 stained thin smears. The smears were fixed with methanol and exposed to a 10% by mass solution of Giemsa-R66 in phosphate-buffered saline solution for ten minutes at room temperature. The thin smears were observed on slides which were rinsed under a stream of tap water and wiped dry with lint-free tissue prior to smearing. The slides were viewed under a light microscope with a 100× objective lens under oil having a viscosity of 1.250 centiStokes, and the parasitised red cells were counted.

The plant extracts were prepared for use by reconstitution thereof, the dichloromethane extracts being initially dissolved in 100 μl of methanol, and then made up to 2 ng/ml with distilled de-ionized water. The stock solutions formed in this way were sterilised using 0.22 μm sterile filter units followed by storage in a freezer at −18° C. until needed for screening.

Microtiter or microdilution plates were used, each consisting of 96 flat-bottomed wells arranged in eight rows (A-H) and twelve columns (1-12). A volume of 100 μl of the culture medium was pipetted into each well, except for the wells of column 3, into which 200 μl of the reconstituted plant extract was pipetted. Two-fold serial dilutions were made of each extract from within the plate, using a multi-channel Eppendorff dispenser. Column 1 was reserved for a red blood cell blank and column 2 was reserved for a parasite control. A volume of 100 μl of a 2% hematocrit (2% by mass of red blood cells) was pipetted into the wells of column 1, and 100 μl of 2% hematocrit and 100 μl of 2% hematocrit with 2% parasitemia (i.e. 2% of the cells were parasitised) were added to the rest of the wells of the plate as a control. The effects of the methanol or other solvent on the parasites were tested, by placing the plates in an airtight desiccator flushed with a gas mixture, by volume, of 3% oxygen, 4% carbon dioxide and 90% nitrogen, in which the plates were incubated at 37° C. for 48 hours.

One of the microtiter/microdilution plates is illustrated in the following table, Table 3. Starting with column 3 in the plate and progressing to column 12, the amount of culture medium was successively halved (i.e. 100% in column 3, 50% in column 4, 25% in column 5 and so forth down to 0.1953% in column 12). The highest concentration of extract, in column 3, was 100 000 ng/ml, and the lowest concentration, in column 12, was 195 ng/ml. The chloroquine was tested at concentrations of 200 ng/ml-0.39 ng/ml. As indicated above, column 1 was employed for a red blood cell blank, and column 2 was employed for a parasite control, a first sample being tested in rows A and B, a second sample being tested in rows C and D, a third sample being tested in rows E and F and a fourth sample being tested in rows G and H.

TABLE 3

|   | 1 | 2 | 3 | 4 | 5 | 6 | 7 | 8 | 9 | 10 | 11 | 12 |
|---|---|---|---|---|---|---|---|---|---|---|---|---|
| A | B | C | 100 | 50 | 25 | 12.5 | 6.25 | 3.125 | 1.5625 | 0.78125 | 0.3906 | 0.1953 |
| B | B | C | | | | | | | | | | |
| C | B | C | 100 | 50 | 25 | 12.5 | 6.25 | 3.125 | 1.5625 | 0.78125 | 0.3906 | 0.1953 |
| D | B | C | | | | | | | | | | |
| E | B | C | 100 | 50 | 25 | 12.5 | 6.25 | 3.125 | 1.5625 | 0.78125 | 0.3906 | 0.1953 |
| F | B | C | | | | | | | | | | |
| G | B | C | 100 | 50 | 25 | 12.5 | 6.25 | 3.125 | 1.5625 | 0.78125 | 0.3906 | 0.1953 |
| H | B | C | | | | | | | | | | |

For antiplasmodial screening a parasite lactate dehydrogenase assay was employed. The test plates were removed from the incubator, and their contents were re-suspended. The wells of another clean 96 well (8 rows×12 columns) microtiter plate had 100 µl of Malstat™ reagent added thereto, for reacting with parasite lactate dehydrogenase. From each of the wells of each plate from the incubator 15 µl of liquid was transferred to the corresponding well in the microtiter plate containing the Malstat™ reagent, and to each of these wells containing the Malstat™ reagent was added 25 µl of a solution of 0.24 mM (milliMolar) phenyl ethyl sulphate (PES) and 1.96 mM nitro blue tetrazoleum (NBT). The formation of a purple colour was an indication of parasite survival. Reaction of the Malstat™ was allowed to take place in the dark for 10 minutes, and absorbence at 620 nm was read in a Model 7520 Microplate Reader manufactured by Cambridge Technology, Inc. Each plate had its well in column 1 containing only red blood cells blanked. The parasite percentage survival was calculated from the absorbence readings using the following formula:

$$\% \text{ parasite survival} = 100 \times \frac{\text{average reading of test wells} - \text{average reading of blank wells}}{\text{average reading of control wells} - \text{average reading of blank wells}}$$

Dose response curves were prepared by plotting the absorbence readings against the concentrations of the extracts, and from these response curves, the $IC_{50}$ was in each case determined, by extrapolation, as the concentration that would inhibit 50% of the parasite population. If desired, standard deviations could be calculated from the absorbence readings.

The extracts showing activity against the malaria parasites were subjected to cytotoxicity studies. Fully attached, confluent cells with a viability greater than 95% were used to assay cytotoxicity.

Microdilution plates were prepared by diluting stock cultures of the extracts with the liquid medium thereof, to a density of 50 000 cells/ml, for use in the MTT cytotoxicity assay described hereunder. A volume of 200 µl of the diluted stock culture containing 10 000 cells was added to each well of a 96 well microdilution plate having 8 rows and 12 columns, except for columns 1 and 2 which served as a blank and a parasite control respectively. Each plate was incubated at 37° C. in an incubator which was continuously flushed with a carbon dioxide atmosphere. The plates were incubated until the cells became confluent.

The extracts were prepared as described above for antiplasmodial screening. In each case the effect of the solvent used to dissolve the plant extract was tested on the cells.

To determine cell viability the cells were trypsinized with a 5% by mass trypsin ethylene diamine tetracetic acid solution in phosphate-buffered saline (PBS) to detach them from the flask in which they were contained. The cells were then spun at 1500 rpm for five minutes in a centrifuge, after which supernatant liquid was aspirated therefrom, and the cells were washed twice with the liquid used as their culture medium. The cells were then re-suspended in culture medium to obtain a cell suspension, and an aliquot of the cell suspension was mixed with an equal volume of trypan blue. After thorough mixing a drop of the mixture was placed in a haematocytometer and covered with a cover slip. The cells were allowed to settle for two minutes, and a count of non-viable cells, namely those which stained blue, were made as a percentage, i.e. the number of cells that stained blue in each hundred cells.

Cytotoxicity was then assayed. When the cells reached confluence, the medium was aspirated therefrom, and 5 ml of said 5% trypsin ethylene diamine tetracetic acid was used to detach them. The cell suspension was centrifuged at 2050 rpm for two minutes, after which the trypsin ethylene diamine tetracetic acid was aspirated and the cells were washed with culture medium. The number of viable cells was counted on a haematocytometer after staining the slide as described above, and the cells were seeded at 10 000 cells/well in the wells of a 96 well flat-bottomed microtiter plate. The cells were allowed to settle and attach for 24 hours, after which the culture medium was aspirated and fresh medium and test extracts were added. The cells were exposed serially to eleven half dilutions of the extracts for 48 hours.

After the 48 hour incubation period 50 µl of a 1 mg/ml solution of [3-(4,5-dimethylthiazol)-2-yl]-2,5-dimethyl-tetrazoliumbromide (MTT) prepared in PBS in all of the wells. The plates were re-incubated for a further 4 hours at 37° C. in an incubator, after which the plates were centrifuged at 2050 rpm for 10 minutes. The culture medium was aspirated in a fume hood. The assay is based on the reduction of the MTT to a purple insoluble formazan product by the reducing enzymes present only in metabolically active live organisms. Formazan crystals were obtained, and 100 µl of dimethylsulphoxide was added thereto in each well, after which the absorbence at 620 nm was read on the abovementioned Microplate Reader, from which cell survival was calculated.

A selectivity index was employed to determine whether or not a given plant extract was to be regarded as cytotoxic or antiplasmodial. To calculate the selectivity index the same units were used for cytotoxicity and antiplasmodial concentrations, according to the following formula:

$$\text{Selectivity Index (antiplasmodial)} = \frac{\text{Antiplasmodial } IC_{50}}{\text{Cytotoxicity } IC_{50}}$$

EXAMPLE 2

Example 1 was repeated with regard to the dichloromethane extract, except that the SPE cartridges were conditioned by washing once with 50 ml of methanol followed by washing once with 50 ml of distilled deionised water (instead of washing thrice with MeCN and then thrice with water as in Example 1). As in Example 1, 4 mg/ml of crude extract was loaded on each column. Bound compounds were eluted at a rate of 17 mL/minute and as detailed above in Table 2, i.e. with mobile phases comprising MeCN and water in the proportions shown in Table 2.

Eluant Fraction 5, 6 and 7, comprising respectively 30% MeCN, 40% MeCN and 50% MeCN, all by volume, contained respectively 0.56±0.065 µg/ml of extract, 0.55±0.12 µg/ml of extract and 0.54±0.11 µg/ml of extract. Each of Eluant Fractions 5, 6 and 7 showed more antimalarial activity than the crude dichloromethane extract.

Pure compounds were obtained by collecting individual peaks from the 40% MeCN fraction (Eluant Fraction 6), which had a number of prominent peaks. A C18 HLPC Haisil 100 semi-preparative cartridge was used, having dimensions of (250×10 mm) and a particle size of 5 µm. A detection wavelength of 215 nm was used, with a flow rate of 2.5 mL/minute, and an injection volume of 216 µl, the mobile phase being an MeCN/water mixture comprising 60% MeCN by volume. This procedure resulted in the isolation of the compounds whose structural formulae are shown respectively in FIGS. 6 and 7. The compound of FIG. 6 was found to display an $IC_{50}$ of 0.19 µg/ml; and the compound of FIG. 7 displayed an $IC_{50}$ of 0.28 µg/ml.

EXAMPLE 3

Figure 8:
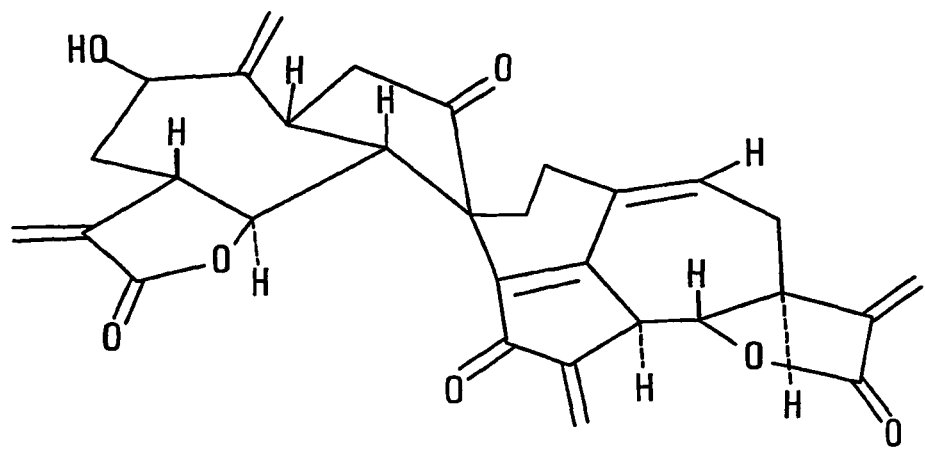
Figure 9:
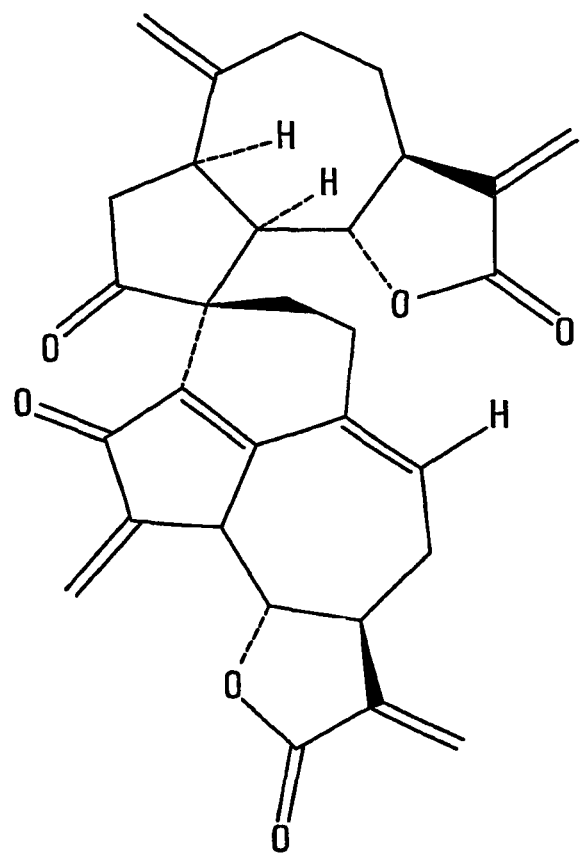

Example 1 was repeated with regard to the dichloromethane extract and, in addition to the compounds of FIG. 2, the compounds of FIGS. 8 and 9 were isolated.

Figure 6:
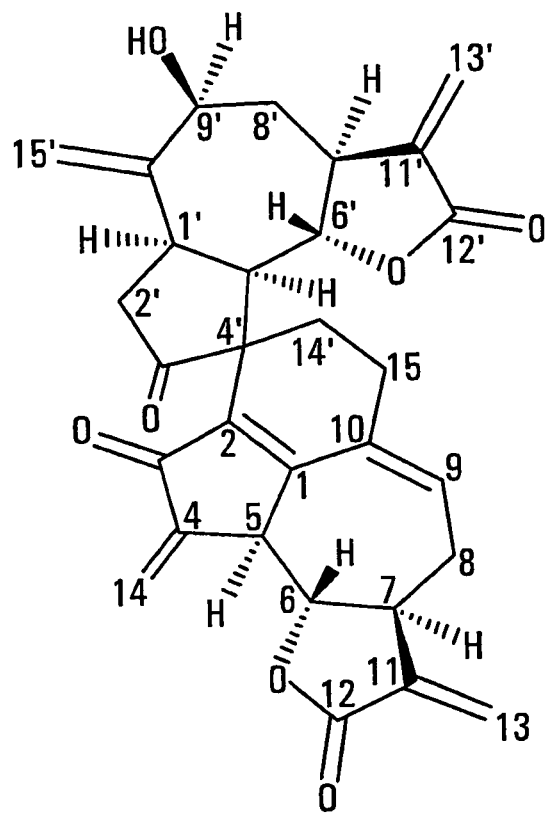
Figure 7:
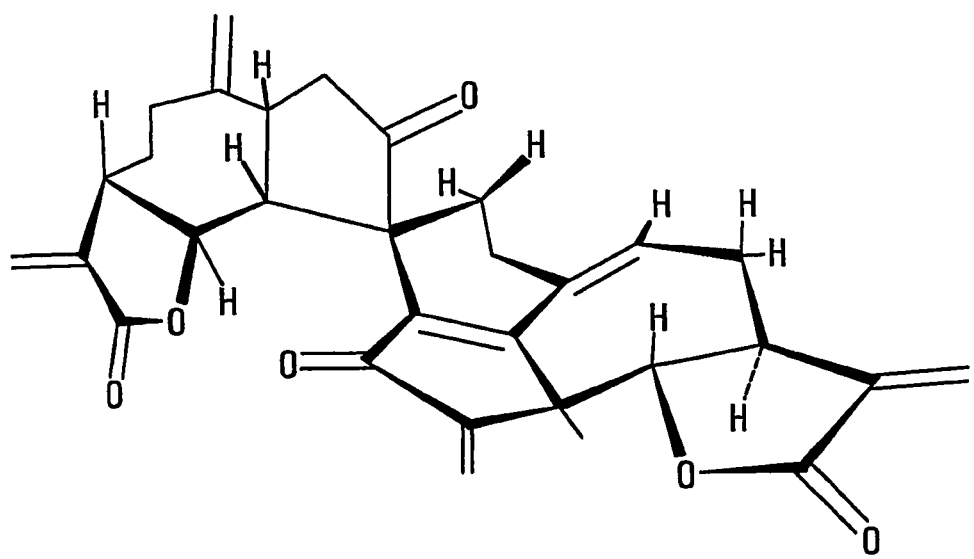

The $IC_{50}$ values of 0.19 µg/ml and 0.28 µg/ml respectively of the compounds of FIGS. 6 and 7 were an approximately ten-fold improvement over the antimalarial activity of the crude extract, being a two-fold to five-fold improvement over the respective fractions from which they were isolated. The compounds of FIGS. 6 and 7 displayed an antiplasmodial selectivity index of 1/2, demonstrating twice as much cytotoxicity as antimalarial activity, but the compounds of FIGS. 6 and 7 were marginally more antimalarially active than the compounds of FIGS. 2, 8 and 9.

It is expected that, for the purpose of treating persons suffering from malaria, the plant extract, or its active ingredients, will be capable of administration by way of one or more of capsules, tablets, syrups, injectable liquids, herbal tinctures (which may be standardised), suppositories, or the like.

The invention claimed is:

1. A dosage form composition for the therapeutic treatment of a parasitic infection in a human or animal, wherein the composition comprises an effective amount of at least one isolated asymmetrical sesquiterpene dimer having a molecular mass in the molecular mass range 230-539 atomic mass units, and wherein the asymmetrical sesquiterpene dimer is extracted from a starting material comprising roots of *Dicoma anomala* by an organic solvent selected from the group consisting of benzene, n-Butanol, butyl acetate, carbon tetrachloride, chloroform, 1,2 dichloroethane, dichloromethane, dioxane, ethyl acetate, di-ethyl ether, methyl-t-butyl ether, methyl ethyl ketone, n-propanol, di-iso-propanol, tetrahydrofuran, toluene, trichloroethylene, and xylene, and wherein the sesquiterpene dimer is selected from a group consisting of one of the following formulae:

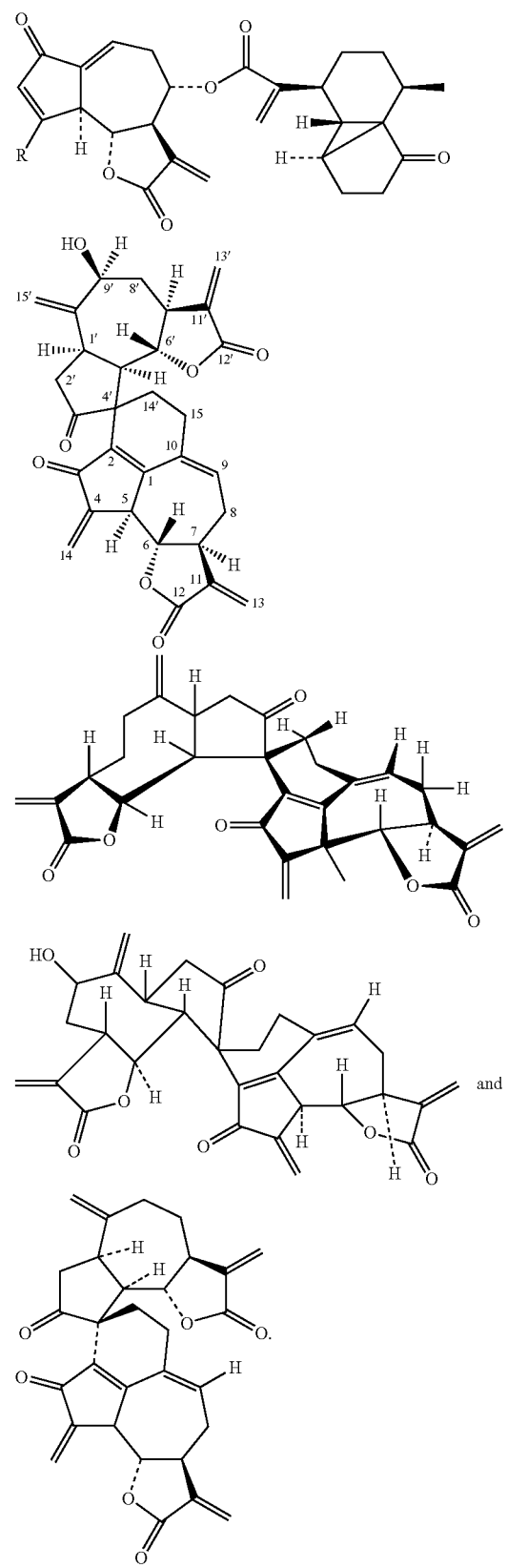

2. The composition of claim 1, wherein the parasitic infection is an infection by the malarial parasite *Plasmodium falciparum*.

3. The composition of claim 1, wherein the parasitic infection is in a human.

4. The composition of claim 1, wherein only one organic solvent is used.

5. The composition of claim 1, wherein the organic solvent is dichloromethane.

6. A dosage form composition for the therapeutic treatment of a parasitic infection in a human or animal, wherein the composition comprises an effective amount of an isolated asymmetrical sesquiterpene dimer as the only anti-parasitic compounds, wherein the asymmetrical sesquiterpene dimer is selected from one of the following formulae:

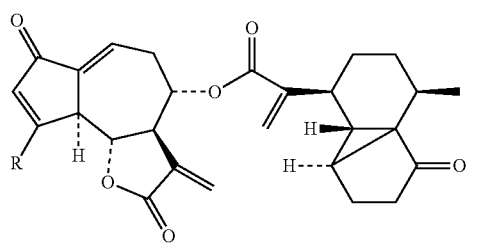

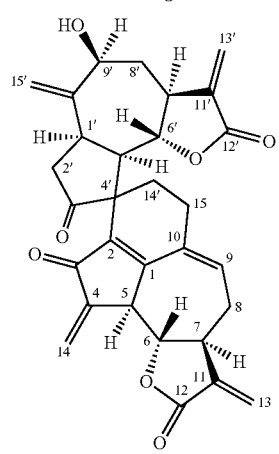

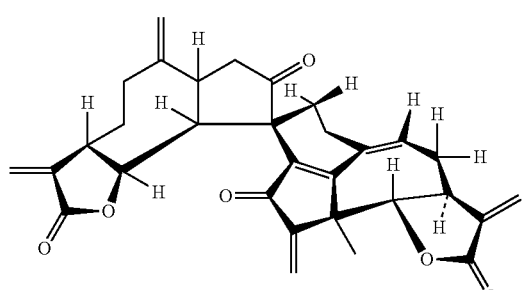

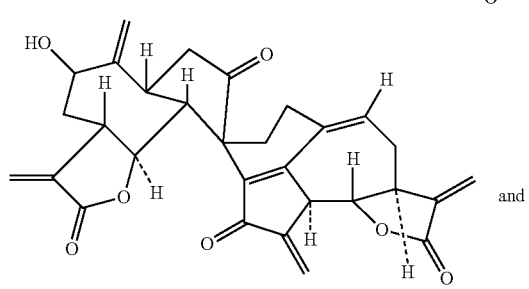

and

-continued

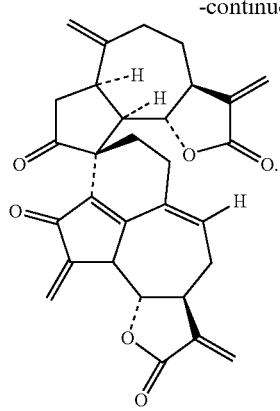

7. The dosage form composition of claim 1, wherein the molecular mass range is between 506 and 508 atomic mass units.

8. The dosage form composition of claim 6 obtained by subjecting roots of *Dicoma anomala* to a first extraction using a solvent comprising hexane followed by a second extraction with dichloromethane.

9. A formulation comprising as an active compound the dosage form composition of claim 1.

10. A formulation comprising as an active compound the dosage form composition of claim 6.

11. A dosage form composition for the therapeutic treatment of a parasitic infection in a human or animal, wherein the composition comprises an effective amount of at least one isolated asymmetrical sesquiterpene dimer as the only anti-parasitic compound wherein the asymmetrical sesquiterpene dimer is selected from one of the two following formulae:

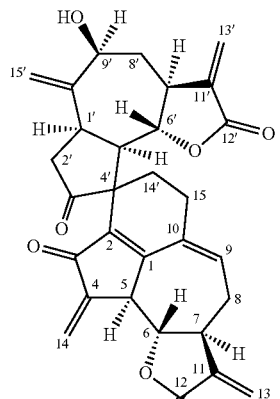

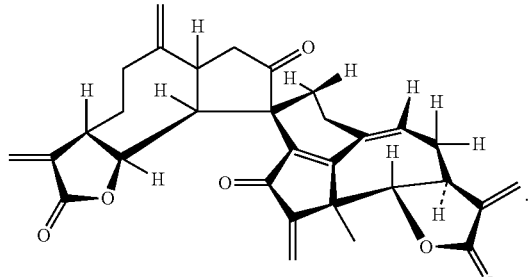

12. A formulation comprising as an active compound the dosage form composition of claim 11.

* * * * *